United States Patent [19]

Maselli et al.

[11] Patent Number: 4,857,339

[45] Date of Patent: Aug. 15, 1989

[54] METHOD FOR MAKING CEREAL PRODUCTS NATURALLY SWEETENED WITH FRUCTOSE

[75] Inventors: John A. Maselli, Winston-Salem, N.C.; Saul L. Neidleman, Oakland, Calif.; Richard L. Antrim, Sparta, N.J.; Richard A. Johnson, Clinton, Iowa

[73] Assignee: Nabisco/Cetus Food Biotechnology Research Partnership, Emeryville, Calif.

[21] Appl. No.: 101,561

[22] Filed: Sep. 28, 1987

[51] Int. Cl.$^4$ .............................................. A23L 1/10
[52] U.S. Cl. ........................................ 426/28; 426/31; 426/44; 426/52; 426/619; 426/621; 426/462; 426/463; 435/94; 435/96; 435/99
[58] Field of Search ............... 435/94, 96, 99; 426/28, 426/31, 20, 52, 619, 620, 462, 463, 18, 44

[56] References Cited

U.S. PATENT DOCUMENTS

| | | |
|---|---|---|
| 897,854 | 9/1908 | Schluter .................................. 426/28 |
| 976,332 | 11/1910 | Anhaltzer . |
| 1,108,555 | 8/1914 | Deming .................................. 426/28 |
| 1,172,270 | 5/1936 | Franzie . |
| 1,178,039 | 4/1916 | Wahl . |
| 1,541,263 | 6/1925 | Hoffman et al. . |
| 1,543,458 | 6/1925 | Takamine .............................. 426/28 |
| 1,564,181 | 12/1925 | Kellogg . |
| 1,568,162 | 1/1926 | Humphrey . |
| 2,040,943 | 5/1936 | Kang . |
| 2,174,982 | 10/1939 | Kellogg . |
| 2,206,619 | 8/1939 | Shreier ................................ 426/621 |
| 2,289,416 | 7/1942 | Fine .................................. 426/28 |
| 2,310,028 | 2/1943 | Gustavson . |
| 2,555,235 | 5/1951 | Huzenlaud . |
| 2,627,464 | 2/1953 | Keahetian . |
| 2,853,388 | 9/1958 | Kiely . |
| 3,157,513 | 11/1964 | Allen et al. . |
| 3,243,301 | 3/1966 | Hesseltine et al. . |
| 3,255,015 | 6/1966 | Blanchon . |
| 3,262,783 | 7/1966 | Blanchon ........................... 426/28 |
| 3,395,019 | 7/1966 | Kviesitis . |
| 3,664,848 | 5/1972 | Bedenk et al. . |
| 3,922,201 | 11/1975 | Hebeda et al. . |
| 3,930,027 | 12/1975 | Kelly et al. . |
| 3,950,543 | 4/1976 | Buffa et al. . |
| 3,956,506 | 5/1976 | Cloud ................................ 426/28 |
| 3,958,015 | 5/1976 | Gay . |
| 3,972,775 | 8/1976 | Wilke et al. . |
| 3,998,978 | 12/1976 | Lawrence et al. ................... 426/285 |
| 4,056,637 | 11/1977 | Hagiwara et al. . |
| 4,069,103 | 1/1978 | Muller . |
| 4,089,745 | 5/1978 | Antrim et al. . |
| 4,247,636 | 1/1981 | Schoenrock et al. ................. 435/96 |
| 4,254,150 | 3/1981 | Fritze ................................ 435/96 |
| 4,282,319 | 8/1981 | Conrad .............................. 426/28 |
| 4,286,058 | 8/1981 | Wenger . |
| 4,292,331 | 9/1981 | Ostre . |
| 4,299,847 | 11/1981 | Morris .............................. 426/18 |
| 4,311,714 | 1/1982 | Goering et al. . |
| 4,371,551 | 2/1983 | Fulger et al. ....................... 426/28 |
| 4,374,860 | 2/1983 | Gasser et al. . |
| 4,377,602 | 3/1983 | Conrad . |
| 4,378,432 | 3/1983 | Castelli et al. . |
| 4,379,171 | 4/1983 | Furda et al. ....................... 426/103 |
| 4,431,674 | 2/1984 | Fulger et al. . |
| 4,435,430 | 3/1984 | Fulger et al. . |
| 4,438,150 | 3/1984 | Gantwerker . |
| 4,451,567 | 5/1984 | Ishibashi . |
| 4,458,017 | 7/1984 | Horwath et al. . |
| 4,500,558 | 2/1985 | Fulger et al. . |
| 4,501,814 | 2/1985 | Schoenrock et al. . |
| 4,540,585 | 9/1985 | Priegnitz . |
| 4,596,776 | 6/1986 | Nonaka et al. ..................... 435/96 |
| 4,613,507 | 9/1986 | Fulger et al. ....................... 426/619 |
| 4,656,040 | 4/1987 | Fulger et al. ....................... 426/28 |
| 4,663,168 | 5/1987 | Von Fulger et al. ................. 426/28 |
| 4,710,386 | 12/1987 | Fulger et al. ....................... 426/28 |

FOREIGN PATENT DOCUMENTS

| | | |
|---|---|---|
| 78782 | 11/1983 | European Pat. Off. . |
| 0124257 | 11/1984 | European Pat. Off. . |
| 0231729 | 8/1987 | European Pat. Off. . |
| 2215467 | 8/1974 | France . |
| 53-62848 | 6/1978 | Japan . |
| 57-47465 | 3/1982 | Japan . |
| WO8605953 | 10/1986 | PCT Int'l Appl. . |
| 622028 | 3/1981 | Switzerland . |
| 1456262 | 11/1976 | United Kingdom . |

OTHER PUBLICATIONS

Reed 1966 Enzymes in Food Processing Academic Press, New York pp. 64–67, 46–49 and 268–272.
Bender 1960 Dictionary of Nutrition and Food Technology Academic Press New York pp. 8–9 and 40–41.
Desrochers et al, *Applied and Environmental Microbiology* pp. 222–228 (1981).
Reed, *Ensymes in Food Processing*, Academic Press, N.Y. pp. 46, 47, 52, 53, 61–67, 88–99 and 269–271 (1966).

*Primary Examiner*—Donald E. Czaja
*Assistant Examiner*—Carolyn Paden
*Attorney, Agent, or Firm*—Richard Kornutik; Albert P. Halluin

[57] ABSTRACT

Breakfast cereals are sweetened by treating cereal grains or at least one cereal grain fraction such as bran, with enzymes comprising glucoamylase and glucose isomerase to produce fructose while retaining cereal particle discreteness or integrity. Enzymatic treatment with alpha-amylase may be initiated prior to, during, or after cooking. The enzymatically treated, cooked cereal grains are formed into breakfast cereal shapes and the enzymes are inactivated to provide a shelf-stable cereal product. The cereal products exhibit a sweet, pleasing complex-honey-like taste and aroma. Producing fructose provides a greater level of sweetness for a given amount of starch conversion into low molecular weight reducing sugars such as mono- and di-saccharides. In achieving a given level of sweetness, more starch or high molecular weight dextrins may be retained for their matrix forming ability or for improved machineability of the enzymatically treated cereal grains into breakfast cereal shapes. The naturally sweetened cereal products of the present invention may be in shredded, flaked, ground, or extruded form.

44 Claims, No Drawings

METHOD FOR MAKING CEREAL PRODUCTS NATURALLY SWEETENED WITH FRUCTOSE

FIELD OF THE INVENTION

This invention relates to the production of breakfast cereals by the treatment of cereal grains or cereal grain fractions with enzymes.

BACKGROUND OF THE INVENTION

Grains provide a rich source of proteins and complex carbohydrates, both of which are necessary ingredients for a well-balanced diet. In addition, grains may be deformed from their discrete shapes into a multitude of forms including flakes, shreds, flours and the like. Starch, composed of both amylose and amylopectin provides for formability of grains into ready-to-eat breakfast cereals, hot cereals, breads, and other baked goods.

Bran, a cereal grain fraction, is relatively low in starch. In the process of U.S. Pat. No. 4,500,558 to Fulger et al, bran is modified by extrusion so that it becomes more readily millable. According to U.S. Pat. No. 4,500,558, from 10 to 25% starch is naturally present or is added to the bran material, the starch functioning as a vapor-lock to build pressure and to coat the bran during extrusion.

Milled grains, cooked or otherwise, generally have a bland and undifferentiated taste. Many schemes have been conceived and protocols designed to treat cereal grains and render their taste sweeter, more complex and more differentiated.

The conversion of grain starches into smaller components has a long history. Hydrolysis of the long polysaccharide chains into shorter chains and monomers such as glucose and maltose may be performed by treating starches with dilute acids, dilute alkalis or by enzymatic catalyzed reactions.

Although there is some evidence for xylose isomerase activity in wheat germ, (Pubols, M. H., et al., Plant Physiology 38, 454 [1962]) and other higher plants (Bartfay, J., Nature 185, 924 [1960]), still, the enzyme would be expected to be denatured during cooking.

Formability and/or product breakage problems tend to arise where grain is altered such that a sufficient amount of maltose or glucose, i.e., dextrose, is produced in sweetening amounts for breakfast cereals. Starch is generally needed for its matrix forming abilities so the grain may be deformed, blended, and conformed into ready-to-eat end products such as shredded wheat, cereal flakes, and expanded or puffed cereals.

In U.S. Pat. No. 4,656,040 to Fulger et al a matrix forming ingredient which is either a modified bran fraction, a toasted ground germ fraction, or combination thereof is admixed with an enzymatically hydrolyzed endosperm fraction. The endosperm fraction, it is disclosed, contains approximately 95% of the starch of the whole grain and treating it alone, with alpha-amylase and glucoamylase, avoids off-flavor development.

Treatment of cereal grains and subcomponents therein with proteolytic enzymes is disclosed in U.S. Pat. Nos.: 1,178,039 to Wahl; 2,853,388 to Kiely; 3,157,513 to Allen et al.; 3,243,301 to Hesseltine et al.; 4,056,637 to Hagiwara et al. Japanese examples of such treatments are taught in: Japanese Patent Publication No. 53-62848, published June 5, 1978; and Japanese Patent Publication No. 57-47465, published Mar. 18, 1982.

In U.S. Pat. No. 1,178,039 a food product is prepared by maintaining a mixture of water and bran at a temperature within the range of 45° C. to 50° C. to produce lactic acid bacteria. The bacteria, it is taught, generate proteolytic enzymes that act on the proteins in the bran. Additionally, diastase, i.e., amylase, contained in the bran inverts gelatinized starch which is added to the mash. The product is used in the preparation of beverages.

U.S. Pat. No. 2,853,388 teaches a process for rendering cereal foods such as corn, rice, wheat, and oats amenable to rapid cooking. The process is carried out by reacting the grains with one or more proteolytic enzymes at 35° C. to 50° C. The cereal, it is taught, may be treated with the enzymes either before or after crushing of the grain.

U.S. Pat. No. 3,157,513 teaches the enzymatic treatment of cereal grains or flour derived from cereal grains to obtain an aqueous liquid material which contains soluble and colloidal partially digested proteins. Grain in finely divided condition is first digested with a proteolytic enzyme in an aqueous slurry to convert more than 50 percent of the protein content of the cereal. The bran and starch residual solids are separated to obtain a proteinaceous liquid. The sludge layer separated from the starch fraction may be subjected to gelatinization and then digested in the presence of amylolytic enzymes to convert the starch content to sugars. The sludge, it is taught, can be simultaneously reacted with proteolytic enzymes to further solubilize and convert any protein portion present.

U.S. Pat. No. 3,243,301 teaches the preparation of tempeh by mixing cereal grains such wheat, rice, and rye with a fungus which produces proteolytic and lipolytic enzymes. The mold, *Rhizopus oligosporus,* has the proprietary designation of NRRL 2710. This mold produces very little or no amylolytic enzymes, thereby avoiding the production of sugars and organic acids. The grains are cracked, soaked with water, inoculated and steamed according to the process.

U.S. Pat. No. 4,056,637 teaches a process for fermenting food products from a cereal germ with lactic acid bacteria. Here, a culture medium containing a water extract of a cereal germ is inoculated with lactic acid bacteria. The water extract is obtained by extracting the cereal germ with hot water in the presence of a starch hydrolase. The starch hydrolase, it is taught, may be used in conjunction with cellulases or proteases. Alpha-amylase, diastase and glucoamylase are taught as suitable hydrolases. The addition of the starch hydrolase, it is taught, leads to the formation of sugars which are required for lactic acid fermentation. The lactic acid fermented product may be dried under conditions which avoid thermal changes to the product. The dried products may be used as such or used as fortifying nutritive additives.

Japanese Publication No. 53-62848 teaches the preparation of a digestible nutritive liquid prepared by immersing a polished rice, rice with germs or a roughly round rice product into an enzyme solution for decomposing indigestible components such as cellulose and hemicellulose. The material is permitted to swell whereupon the solid material is separated from the enzyme solution. Water is then added followed by boiling to obtain a liquid food. The enzymes used, it is taught, may be cellulase, pectinase, or hemicellulase. A nutritive food, such as bean milk may be added with protease to the solid material which is separated from the enzyme solution.

Japanese Publication No. 57-47465 teaches the preparation of a cereal tea extract. In this process, cereal grains are heated at 110° C. to 200° C. to vaporize their undesirable flavors and to puff their albumin content. The heated cereal grains are impregnated with an aqueous solution containing at least one kind of enzyme selected from amylase, protease, and cellulase. The impregnated cereals are heat-dried at 50° C. to 100° C. and then roasted at 100° C. to 170° C. The heating, it is taught, causes puffing which allows impregnation of the enzyme solution into the cereal grains. However, none of the above cited references teach the production of shredded, flaked, or extruded cereals.

The production of cereal products which may be in shredded, flaked or extruded form by treatment of cereal grains with proteolytic enzymes is taught in U.S. Pat. Nos.: 976,332 to Anhaltzer; 1,541,263 to Hoffman et al.; 3,664,848 to Bedenk et al.; and 4,282,319 and 4,377,602 to Conrad.

U.S. Pat. No. 976,332 teaches making breakfast cereals from wheat, corn, rye or other grains by mixing flour with an aqueous solution of pepsin, i.e., a proteolytic enzyme. Here, dough is used to form a film which is then dried and roasted. A flavorant, including desiccated coffee and sugar, is added as a coating to the roasted flake.

U.S. Pat. No. 1,541,263 teaches defatting the germs of cereals such as wheat germ, maize germ or rice polishings, i.e., germ and bran material, cooking them to gelatinize the starch, and then treating them with malt, i.e., diastase enzyme, to convert the starch in the grain to maltose and dextrin. Also, proteolytic enzymes, e.g., papain, trypsin, pancreatin, and pepsin, are added singly or in combination. The dried product may be used as an ingredient in the preparation of bread or shredded or flaked cereals.

U.S. Pat. No. 3,664,848 teaches the preparation of a breakfast cereal by mixing a soy protein source, proteolytic enzymes and a pregelatinized grain to form a dough. The dough is used to form strands which are then pelletized. The pellets are then puffed. Extrusion and flaking are taught as well.

U.S. Pat. Nos. 4,282,319 and 4,377,602 teach processes for preparing, in situ, enzymatically hydrolyzed protein and starch products from whole grain. The processes comprise crushing whole grain and thereafter subjecting the crushed grain to an enzymatic treatment in an aqueous medium with an endopeptidase so as to transform substantially all of the water soluble proteins to water soluble protein products. The water soluble starch fraction in the remaining crushed grain is subjected to enzymatic treatment in an aqueous medium with at least one starch hydrolyzing enzyme to transform substantially all of the water and soluble starch fractions to water soluble degraded products of starch. The processes are preferably carried out below the gelatinization temperatures of the grain. Bran may be removed either before or after enzymatic treatment of the cereal. The final cereal product may be used as a nutrient in breakfast flakes. Sequential treatment with alpha-amylase, amyloglucosidase and isomerase to form fructose may be used to solubilize the starch. The pH at which the amyloglucosidase acts is used to control hydrolysis to maltose or glucose. In Example 22, production of a breakfast cereal product containing wheat syrup and bran is disclosed. The wheat bran is obtained by isolation from a crushed grain which has been enzymatically hydrolyzed with protease, amylase, and amyloglucosidase. (See Example 2.) Enzymatic treatment of substantially only bran in the production of a cereal is not taught.

In these processes for producing cereal products using proteolytic enzymes, a whole cereal grain or a bran fraction is not treated enzymatically so as to retain starch or high molecular weight dextrins for their matrix forming ability.

The enzymatic treatment of cereal grains using cellulase or a combination of alpha amylase, amyloglucosidase, and glucose isomerase are disclosed in U.S. Pat. Nos.: 4,069,103 to Muller; 4,089,745 to Antrim et al.; 4,247,636 to Schoenrock et al.; 4,292,331 to Ostre; 4,378,432 to Castelli et al.; 4,458,017 to Horwath et al.; and 4,501,814 to Schoenrock et al. Processes using starch attacking enzymes are also taught in European Patent Application No. 78,782 and Swiss Patent Publication No. 622,028, published Mar. 13, 1981.

U.S. Pat. No. 4,069,103 teaches a process for obtaining dextrose and dextrins from a proteinaceous starch product. The starch product is subjected to acid or enzymatic hydrolyses whereupon the proteins are separated from the sugar solution using an ultrafiltration method. High molecular weight soluble protein is recovered and then subjected to spray drying to obtain a high protein product. The sequential treatment of starch with an amylase, amyloglucosidase, and isomerase is also taught.

U.S. Pat. No. 4,089,745 teaches a process for enzymatic conversion of corn hull cellulose to glucose wherein corn hulls are treated with alkali to obtain three fractions and cellulose is converted enzymatically to glucose.

U.S. Pat. No. 4,247,636 teaches the production of a fructose sweetener from an impure starch source containing beta glucans. Here, impure flour and water are mixed and then treated with the enzyme beta glucanase to produce a slurry having a viscosity of less than about 1,000 centipoise. The slurry is then sequentially treated with alphaamylase, glucoamylase, and glucoisomerase. Conversion of starch solutions into high fructose sweeteners using a three-enzyme process is taught as old in the art.

U.S. Pat. No. 4,292,331 teaches a process for stabilizing and preserving harvested vegetables in an acidic environment located within a silo. The desired acidity is obtained by degradation of starch, complex carbohydrates, and fermentable carbohydrates. A mixture of bacteria and enzymes capable of degrading complex carbohydrates into fermentable sugars is used. Here, fermentable sugars are fermented into lactic acid by lactobacilli. Enzymes which may be used include a mixture of fungic amylases, amylases of bacterial origin, amyloglucosidases and hemi-cellulases. The enzymes may be supported on a cereal, preferably in a finely ground form. The starch contained in the support is added to the starch in the carbohydrates contained in the vegetables and is degraded into fermentable sugars. The process, it is taught, makes it possible to completely restrain all butyric fermentation.

U.S. Pat. No. 4,378,432 teaches the production of a sweetened aqueous liquor from a cellulose-containing vegetable substrate. Here, a vegetable substrate is treated with phosphoric acid under conditions causing hydrolysis of the cellulose contained within the substrate. Next, an enzyme is added to the resulting product to hydrolyze cellulose to form an additional amount of reducing sugars so as to obtain a sweetened aqueous liquor. Enzymes which hydrolyze cellulose and hemi-cellulose are used.

U.S. Pat. No. 4,458,017 teaches the preparation of fructose by liquefying starch with alpha-amylase, contacting the resulting liquefied starch with glucoamylase, and isomerizing at least part of the glucose to fructose using glucose-isomerase. All three enzymes are obtained from the same organism, i.e., *Irpex mollis*. References relating to the enzymatic conversion of glucose to fructose are listed in column 1, lines 40 to 56.

U.S. Pat. No. 4,501,814 teaches the production of a high fructose sweetener from an impure starch flour. The flour is subjected to enzymatic degradation in a sequence of steps which first liquefies, then saccharifies, then purifies the liquid starch. Substantially all the undissolved matter is removed from the slurry subsequent to initiation of the saccharification stage but prior to complete saccharification. Roughage, such as grain hulls, is removed mechanically prior to slurrying the impure starch flour. Beta-glucanse and alpha-amylase are added sequentially to the slurry to liquefy the starch. The production of high fructose corn syrups by treatment of starch solutions with alpha-amylase, glucoamylase, and glucoisomerase in sequential fashion is taught as old in the art. Several expired patents directed to such processes are listed at column 1, line 45 to column 2, line 15.

European Application No. 78,782 teaches the enzymatic treatment of whole cereal grains for the production of beer by a heat-technical wet processing method. Here, glucose is produced which reacts with proteins to form glucoproteins. The production of glucoproteins, it is taught, should be avoided because they are difficult to digest. Accordingly, alpha-amylase and ground cereal grains are added simultaneously to water having a temperature such that starch is only converted to soluble dextrins and oligosaccharides before inactivation of the enzyme by heat. Treatment of the starch with alpha-amylase at such a temperature, it is taught, avoids glucose production as well as the formation of sugar-protein compounds. The liquid phase which is obtained may be further treated to decompose the starch derivatives using amyloglucosidase and/or isomerase.

Swiss Pat. No. 622,028 teaches a process for producing foodstuffs having a desired level of sweetness obtained without the addition of sweeteners. Such products can be cocoa. The raw materials can be ground cocoa beans, boiled potatoes or boiled potato waste, or broken baker's wares. In a specific example, cocoa powder is treated with alpha-amylase, amyloglucosidase and isomerase. Fifty percent of the cocoa starch was converted to fructose. When the dispersion was dried, the resultant cocoa powder had 50 percent of the original starch converted to glucose and 50 percent to fructose. The starting materials are ground or mechanically manipulated so as to expose the starch thus destroying the integrity of the starting materials.

However, the products resulting from these enzymatic treatments with cellulase or alpha amylase, glucoamylase, and glucose isomerase are not cereals. Retention of starch for its matrix forming properties so as to provide formability of the enzymatically treated cereals is not taught in these references.

Enzymatic treatment of ground grains or grain fractions with sugar-producing enzymes in the preparation of cereal products is taught in U.S. Pat. Nos.: 1,172,270 to Franzie; 2,040,943 to Kang; 2,289,416 to Fine; 3,255,015 to Blanchon; 3,395,019 to Kviesitis; 3,930,027 to Kelly et al.; 3,950,543, to Buffa et al. and 4,311,714 to Goering et al.

In U.S. Pat. No. 1,172,270 a food product is produced by fermentation of ground, cooked rice or other cereals with a fruit extract or fruit such as banana. The starch within the rice is converted to a sugar.

U.S. Pat. No. 2,040,943 teaches preparing sweet tasting cereal foods by mixing rice, ground wheat, and ground malted barley, then boiling the mixture. After boiling, the mixture is simmered and liquid is recovered which is then boiled until thick. The liquid is then cooled and pulled. An analysis of the finished product shows the presence of sucrose, dextrins, and reducing sugars. (See the second column in the patent.)

U.S. Pat. No. 3,255,015 teaches the treatment of the envelope and cortical layer of cereal grains for the purpose of separating the enzymes and nutrients. Bran, it is taught, may be treated for release of enzymes, enzyme activators, oliogoelements and sugars. Here, an initial batch or charge consisting of the envelope and cortical layer of cereals are treated enzymatically so as to obtain a liquid rich in enzymes and other active substances. The liquid is continuously recycled so that the envelope and cortical layers of the cereal grains are subjected to continuous treatment. In the preferred embodiment, five parts water is mixed with one part ground bran. The aqueous bran mixture is then treated with pectinolytic enzymes obtained from fungi, bacteria or cereal brans. In one arrangement, a cellulose residue is strongly attacked by the enzymes contained in the plant tissues. The enzymes, cellulase and hemi-cellulase, are either added per se or after a preserving treatment. Food products such as cakes, oils rich in cellulose, fish waste, etc. are produced.

U.S. Pat. No. 3,395,019 teaches a process for making animal feed from oat hulls. Ground oat hulls are mixed with water in an amount of 50 to 70 percent by weight, followed by treatment with alkali and yeast or enzymes such as catalase, cellulase, and amylase. The treatment of the oat hulls, it is taught, increases the absorption capacity of the hulls for materials such as molasses, fish solubles and the like.

U.S. Pat. No. 3,930,027 teaches a process for making precooked dehydrated products. Here, gelatinized starch is reacted with amylase until complete hydrolysis occurs. Then, the hydrolyzed starch is slurried with some nonhydrolyzed starch such that a maltose concentration of about 14 percent, based upon the total weight of the slurry, is obtained. The concentration of maltose is critical, it is taught, for reducing susceptibility to caking. Reconstitution of the hydrated, flaked product results in a homogeneous smooth textured cereal mass.

U.S. Pat. No. 3,950,543 teaches a process for making weaning flour or baby foods. Here, a material such as flour, meal, grits and cereal is mixed with at least one high temperature resistant starch-hydrolyzing enzyme. The mixture is then heated in the range of 65°–115° and simultaneously extruded. The extrudate is fermented to a dextrin and reducing sugar concentration of 25 percent and 15 percent respectively, based on the initial starch content. The patent discloses a two-enzyme process, wherein the enzymes are alpha-amylase and glucoamylase.

U.S. Pat. No. 4,311,714 teaches a process for making protein products and maltose syrup from flour obtained from a waxy barley grain. Beta-glucans contained in barley starch solids are partially hydrolyzed. Proteins are released and starch is at least partially hydrolyzed to obtain maltose. One of the enzymes used in the hydrolysis is amylase. The barley starch solids which are treated with the enzyme have at least a portion of the protein solids removed from the starch. Use of a wax grain, it is taught, is critical because of amylopectin content. The beta-glucans are removed to facilitate working on the barley. Bran, a by-product, is separated from the grain and not subjected to the enzyme treatment.

However, in the processes of these patents, the enzymatically treated ground grains or grain fractions are not taught as being formed into flaked, shredded, or extruded cereals.

The production of instant breakfast cereals in powdered or flaked form involving the enzymatic treatment of ground grains or grain fractions with sugar producing enzymes is disclosed in U.S. Pat. Nos. 4,374,860 to Gasser et al and 4,438,150 to Gantwerker.

U.S. Pat. No. 4,374,860 teaches the baking of a readily water-miscible powdered amylaceous food product. Here, a mixture of materials such as coarse meal, fine flour, cereal starch, and water is cooked to cause gelatinization of the amylaceous material while liquification of the mixture is brought about by enzymatic hydrolyses. Additional amylaceous material is added to the mixture whereupon this second mixture is cooked to cause gelatinization. This second mixture is liquefied by enzymatic hydrolyses and then spray dried. The enzymatic hydrolysis employs alpha-amylase, amyloglucosidase or beta-amylase. Hydrolysis using amyloglucosidase without alpha-amylase is taught as being slower in starting but results in a higher degree of hydrolysis. The resultant product is a powder which is suitable for use in soups, acidic beverages or instant breakfasts. The process avoids expensive concentration steps and Maillard or carmelization reactions. The browning reactions, it is taught, occurs in known processes involving the production of instant flaked cereals where a paste or suspension of ground cereal is gelled and enzymatically hydrolyzed on a drying drum.

U.S. Pat. No. 4,438,150 teaches a process for making a dry, gelatinized cereal porridge product capable of being instantly prepared as a hot or cold food. Here, a gelatinized cereal flour slurry is subjected to mechanical shear of sufficient intensity and duration so as to reduce viscosity of the gelatinized cereal mixture. The patent teaches away from the use of enzymes to reduce viscosity because browning reactions between cereal protein and glucose, excessive flake product density, and production of a watery porridge upon reconstitution occur.

The enzymatic treatment of ground grains or grain fractions with sugar-producing enzymes in the production of a ready-to-eat (RTE) cereal in shredded, flaked, or extruded form is disclosed in U.S. Pat. Nos.: 1,564,181 to Kellogg; 1,568,162 to Humphrey; and 4,431,674 and 4,435,430 to Fulger et al.

In U.S. Pat. No. 1,564,181 a bran food is prepared by mixing ground barley malt (a source of malt enzymes) with bran to convert bran carbohydrates to maltose or malt sugars. Winter wheat bran is taught as being preferred. Following enzymatic treatment, the mixture is cooked, dried, then shredded or flaked. Other enzymes may be substituted for the malt enzymes, it is taught. The dried bran is shredded at a moisture content of 10 percent or 20 percent. The shredded product is then preferably dried or toasted. Flaked products are produced by allowing the dried bran to stand and harden. Lumps are formed and then broken into smaller pieces. The pieces are then rolled into flakes and dried or toasted. The dried bran may be ground and then toasted or dried in powder form as well. Biscuits may be formed from the powdered or shredded product.

U.S. Pat. No. 1,568,162 teaches a process for making cereal which is a combination of a fruit pulp, e.g., apples, and a grain such as wheat. Yeast is added to produce fermentation of the starch although this action is limited to prevent conversion of carbohydrates to alcohols. Fruit pulp, sugar, yeast, and flour are mixed to form a dough.

The dough is left in a warm atmosphere for 30–40 minutes, then cooked. The dough is then formed into pieces using a die. The pieces are then dried, flaked and toasted.

U.S. Pat. Nos. 4,431,674 and 4,435,430 teach the preparation of enzyme-saccharified ready-to-eat breakfast cereals derived from whole cereal grains. The process comprises the steps of: (a) milling and separating a whole cereal grain to produce a germ fraction, a bran fraction and endosperm fraction; (b) enzymatically hydrolyzing from 15 to 75 percent by weight of the endosperm fraction; (c) modifying the bran fraction to improve its functionality; and (d) recombining the treated fractions to form a cereal dough. These patents teach that it is critical to treat bran fractions to improve functionality and that subjecting all of the cereal substances to enzymatic treatment makes it difficult to produce a dough of sufficient functionality. A dual simultaneous enzymatic reaction involving bacterial alpha-amylase and fungal glucoamylase is preferred. The recombined fractions may be formed into flakes and cut into shapes with a cookie cutter. They may also be combined with an endosperm or starch fraction then expanded.

In the production of these ready-to-eat cereals and instant breakfast products using sugar producing enzymes, enzymatic treatment so as to retain starch and high molecular weight dextrins for matrix forming ability while developing sweetness and taste complexity is not taught.

The enzymatic conversion of whole cereal grains with sugar producing enzymes in the preparation of cereal products is disclosed in: U.S. Pat. No. 2,310,028 to Gustavson; U.S. Pat. No. 2,555,235 to Huzenlaud; U.S. Pat. No. 2,627, 64 to Keahetian; U.S. Pat. No. 3,958,015 to Gay; U.S. Pat. No. 4,371,551 to Fulger et al and Japanese Patent Publication No. 37-1654.

U.S. Pat. No. 2,310,028 teaches a process for making canned cereal such as oatmeal, wheat porridge, or corn meal. Cereal such as steel-cut dry oat meal or rolled oats, is precooked with water. A diastase enzyme is added to the cooled mixture to digest the starch. The mixture is then heated to sterilization temperatures and then sealed. Typically, the oat porridge is stirred slowly while being digested by the added malt diastase enzymes for about two minutes at 126° F. The temperature is raised to 149° F. to stop enzymatic activity.

U.S. Pat. No. 2,555,235 teaches a process for enriching the endosperm of grain by applying a vacuum to the grain which is then steeped in an extract of grain or offal to add more vitamins and minerals. Steeping takes place at a temperature and pressure which promote enzymatic action. Diastase or other enzymes may be added to promote enzymatic action. The grain is then treated with live steam and dried for milling or packaging. A list of the enzymes present in the grains is enumerated in column 5 of the patent. The first five enzymes of the list include amylase, glucosido and fructosido saccharases as well as the glucosido and gluco maltases. Cellulase is also listed.

U.S. Pat. No. 2,627,464 teaches a process for making breakfast cereals such as baby food. Wheat is germinated until the sprouts reach a length of about one-half inch. The germination is stopped by drying the sprouts. The dried sprouts are then ground into flour which is then mixed with water to form a dough-like consistency. The dough is then slowly cooked. Enzymes, it is taught, develop in the grain during the germination stage. These enzymes act on the starch during slow cooking which occurs in the temperature range of 180° F. to 200° F. for as long as eight hours. After cooking, the product is canned for long term storage.

U.S. Pat. No. 3,958,015 teaches a process for treating plant materials to obtain an augmented high protein and low carbohydrate product. Plant materials having a high level of starch are treated with enzymes which modify the carbohydrates to forms assimilable by yeast. Metabolism by elementary yeast enriches the protein content over that of the starting material. The plant material may include partially or completely dehulled soybean, legume beans, cereals, roots and tube roots. The plant materials, which have or have not been thermally treated, dehulled, peeled, ground, crushed, or flattened are subjected to the simultaneous action of enzymes. The enzymes used are the amylases, pectinases, cellulases, invertases, and beta-glucanases. The treatment of fine flour obtained from dehulled small white beans with alpha-amylase, betaglucanase, amyloglucosidase, and invertase is taught in Example III. After treatment with yeast, the reducing sugar content is less than one percent in the final dried product.

U.S. Pat. No. 4,371,551 teaches producing a composition possessing a malt-like flavor from root cultures and the use of the composition in a foodstuff such as breakfast cereal. A cereal grain, it is taught, upon germination, produces starch splitting enzymes such as alpha- and beta-amylase. In the process of U.S. Pat. No. 4,371,551 the rootlets are cultured and contain highly concentrated malt-like flavors.

Japanese Patent Publication No. 37-1654 teaches a process for making auto-digestive cereals such a malts. The cereals are steamed after having their pH adjusted for enzymatic reactions. Enzymes are then added which have been treated so as to be active at less than 55° C. An edible salt is then sprayed on the material which is then dried.

However, in these processes for producing cereal products by enzymatically converting whole cereal grains with sugar producing enzymes, forming enzymatically treated grains into ready-to-eat cereals in shredded, flaked, or extruded form is not taught.

Production of a ready-to-eat cereal in shredded or flaked form involving enzymatic treatment of whole cereal grains with sugar producing enzymes is disclosed in U.S. Pat. Nos.: 2,174,982 to Kellogg; 2,289,416 to Fine; and 4,254,150 to Fritze et al.

U.S. Pat. No. 2,174,982 teaches a process for making shredded or flaked cereal foods from cereal grains such as wheat, rye, corn or oats. Here, the whole grain is boiled in alkali to partially dissolve the bran coating. The grain is then washed to remove the alkali and then treated with malt to convert starch to dextrins. A flavoring substance is added to the wort, whereupon the wort is kept at 148° F.–170° F. to expand the grain and allow penetration of the flavoring substance. The material is then cooked under pressure, dried and either flaked or shredded. The moisture content of the material for shredding is 20 percent. The dextrins in the product, it is taught, make it crisper. U.S. Pat. No. 2,289,416 teaches a process for making cereal foods in flaked or shredded form from whole grains. Prior to enzymatic action, the whole grains are treated by rupturing of the bran coat and gelatinization of starch with heat. Following this pretreatment, enzymes are added directly to the whole grain. The enzymes, it is taught, act more rapidly on gelatinized starch. Malted grain is taught as an enzyme source. Efficient conversion of gelatinized starch is taught as being at a temperature of from 60° C. to 70° C. Bumping, it is taught, greatly increases the permeability of the endosperm which can be performed before or after the gelatinization step. The addition of enzyme to flour and to bumped grain prior to cooking is taught as resulting in no substantial conversion of starch to subcomponents. Malted barley flour and a diastase concentrate, i.e., an *Aspergilius oryzae* amylase preparation, are each used as enzyme sources. Maltose is the only specifically disclosed sugar which is produced by this process.

U.S. Pat. No. 4,254,150 teaches the production of cereal foods in flaked form. Here, starch, in situ, is converted to dextrose by enzymatic conversion. Whole grains or grains ground from coarse to medium-fine grist is mixed with water to form a mash with the grain fraction of the mash being 20 to 40 percent. The mash is allowed to swell whereupon alpha-amylase is added. The pH of the mash is adjusted. The mash is then heated in a steam injection cooker at a temperature in the range of 100° C. to 110° C. The mash is then passed through a tube type converter which is also maintained at a temperature to 100° C. to 110° C. At this point the starch is converted to maltodextrin. The enzyme amyloglucosidase is then added to the mash to effect the conversion of maltodextrin to dextrose. The mash is then dried on a single roll dryer to form a thermoplastic film. The film is cooled to make it friable and then comminuted to form flakes. Prior to drying the mash, bran or other additives may be added for the production of a fodder. The enzymatic degradation of the starch in the grain is achieved without separating the starch from the grain or from the other dry substances such as glutin, fibers, and husks.

In the production of these ready-to-eat cereals, the enzymatic treatment of the whole cereal grains with sugar producing enzymes is not taught as retaining starch and high molecular weight dextrins for their matrix forming properties while developing sweetness and taste complexity.

The present invention provides a process for the production of breakfast cereals which are enzymatically sweetened while retaining starch and high molecular weight dextrins for their matrix forming properties. In the present invention, the in situ production of fructose requires less starch conversion to achieve a desired level of sweetness. The production of fructose also provides enhanced, honey-like, graham, flavors and aromas in the breakfast cereals of the present invention. Reduced starch breakdown provides for improved formability of the enzymatically treated cereal grains into breakfast cereal shapes and improved shape retention at a given level of sweetness.

SUMMARY OF THE INVENTION

The present invention provides a process for the production of breakfast cereals which are sweetened by the enzymatic conversion of starch to fructose. Conversion to fructose provides enhanced, honey-like, graham flavors and aromas to the cereal products of the present invention. In addition, to achieve a desired level of sweetness, less conversion of starch or less breakdown of high molecular weight dextrins is needed because of the higher sweetening power of fructose compared to other reducing sugars. Accordingly, a larger proportion of starch and higher molecular weight dextrins can be retained for matrix formation or machineability of the enzymatically treated cereal grains. In addition, shape retention of the breakfast cereals is enhanced at a given sweetness level as the proportion of retained starches and/or high molecular weight dextrins increases.

In the present invention, cereal grains or at least one cereal grain fraction is cooked with water to at least partially gelatinize the cereal starch. The enzymatic treatment may begin prior to cooking, simultaneously with cooking, or subsequent to cooking. The amount of water used during the enzymatic treatment is preferably limited so that at least substantially all of the water is absorbed by the cereal grain thereby reducing loss of sugars upon draining of the cooked grains. The cooking of the cereal grains or the cereal grain fraction and the enzymatic treatment are performed so that the discreteness or integrity of the grains or particles is substantially retained. This permits formation of the enzymatically treated particles into breakfast cereal shapes using conventional, mass production cereal forming equipment.

In the present invention, glucoamylase is used to form dextrose. A portion of the dextrose is converted to fructose by the use of glucose isomerase. The glucoamylase and glucose isomerase are added simultaneously or sequentially. The glucoamylase and glucose isomerase are preferably added after cooking to avoid premature inactivation of these enzymes. In the present invention, alpha-amylase may be used to convert the starch to dextrins. The alpha-amylase may be added simultaneously with or prior to addition of the glucoamylase and glucose isomerase.

The enzymatically treated cereal grains may be incubated or tempered up to about 48 hours, typically from about 2 to about 24 hours. The tempered product is then drained, and formed into breakfast cereal shapes. The enzymatically treated cereal grains may be formed by shredding, flaking, grinding, extrusion, and the like. The enzymes are inactivated by heating of the formed cereal. Enzyme inactivation may also be initiated prior to or simultaneously with the forming step.

The amount of fructose produced by the enzymatic conversion of the starch is sufficient to provide a sweet taste in combination with the other reducing sugars produced during the enzymatic treatment. The fructose which is produced also provides a honey-type or graham cracker-type taste and aroma. The fructose content of the cereal products of the present invention is at least about 1% by weight, preferably at least about 5% by weight, based upon total dry solids. The reducing sugar content of the cereal products of the present invention may range up to about 35 percent by weight, suitably from about 10% to about 25% by weight, based upon total dry solids. The amount of fructose which is produced by the enzymatic conversion may range from about 5% to about 45% by weight, suitably from about 15% to about 40% by weight, based upon the total weight of monosaccharides of the cereal product.

DETAILED DESCRIPTION OF THE INVENTION

The cereal products of the present invention are naturally sweetened with reducing sugars comprising fructose. Naturally occurring starches present in cereal grains or cereal grain fractions are enzymatically altered to provide sweetening and taste complexity and pleasant aromas in the final product.

The cereal grains which may be used in the present invention are wheat, oats, rice, corn, barley, rye, combinations thereof, and the like. The preferred cereal grain is wheat. The grains may be bumped or unbumped. Bumped grains provide for more rapid penetration by the enzymes which results in shorter conversion times. Cereal grain fractions which may be used in the present invention include any comminuted products or meals derived from cereal grains. They include a bran fraction, an endosperm fraction, a germ fraction, portions thereof, or mixtures thereof such as flour or whole wheat flour. The cereal grain fraction may be obtained by conventional milling, classification, and blending processes.

The at least one cereal grain fraction should generally contain at least 10% by weight of cereal starch, suitably from about 25% to about 45% by weight, on a dry weight basis. The preferred cereal grain fraction is wheat bran. The starch content of the bran may range up to about 60% by weight of naturally occurring and/or added cereal starch. A higher starch content, suitably from about 45% to about 55%, permits the production of higher amounts of fructose in the cereal product.

The cereal grains may be cut, suitably steel cut, whole cereal grains, or germinated or malted grains. Whole berries are preferred for the production of shredded cereals and flaked cereals.

In the present invention, the enzymatic conversion is conducted so as to retain the discreteness or integrity of the cereal grains. It is also preferred to maximize the amount of fructose as a percentage of the total reducing sugars provided it does not create excessive sweetness, or adversely affect machineability or product color. In the treatment of a cereal grain fraction, the integrity of the particles, such as bran, should also be retained. Retention of the integrity or discreteness of the cereal grains or particles and retention of starch or high molecular weight dextrins is needed for formability or machinability into breakfast cereal shapes on conventional processing equipment. For example, in the production of shredded wheat, the enzymatic treatment of whole berries should not destroy the integrity or discreteness of the berry. If discreteness is destroyed, the grains tend to clog shredding roll feed hoppers and tend to stick to the shredding rolls. The retention of starch or matrix-forming high molecular weight dextrins, should be sufficient so as to provide machineability and formability as well as to provide resistance to breakage in the final cereal product.

In the present invention, D-xylose ketol-isomerase, also known as xyose isomerase, but more commonly known as glucose isomerase is used to convert glucose to fructose. The glucose is produced by the use of amyloglucosidase or glucoamylase, also known as amylo-1,6-glucosidase. The glucoamylase may produce glucose by enzymatic conversion of starch or by enzymatic conversion of dextrins derived from the cereal grain starch. The dextrins may be obtained by enzymatic treatment of the cereal grains or at least one cereal grain fraction with an alpha-amylase. Alpha-amylases hydrolyze starch molecules at alpha-1,4-hemiacetal (—C—O—C—) links randomly, whereas cleavage by glucoamylase yields glucose. Accordingly, cleavage by glucoamylase produces more reducing sugar while retaining higher molecular weight dextrins for their matrix forming ability. In the present invention, the use of alpha-amylase is optional.

In the present invention, the optional alpha-amylase is admixed with the cereal grains or at least one cereal grain fraction and water either prior to cooking, at the initiation of cooking, or after cooking. When the alpha-amylase is added prior to cooking, the cereal grains or at least one grain fraction is soaked in the presence of alpha-amylase suitably at a temperature of from about 68° F. (20° C.) to about 212° F. (100° C.). Suitable soaking times range from about one-half hour to about four hours.

The cereal grains are cooked in the presence of water and the optional alpha-amylase to at least partially gelatinize the starch. The degree of gelatinization is typically complete. By complete gelatinization it is meant that there is a complete absence of birefringence and complete absence of enthalpy of gelatination by differential scanning calorimetry.

Cooking temperatures generally range from about 176° F. (80° C.) to about 212° F. (100° C.). Cooking times generally range from about 15 minutes to about 45 minutes. The pH during presoaking or cooking is suitably from about 5 to about 8. Generally the cooking times and temperatures should be sufficient to completely eliminate white centers or to leave only faint white centers in the berry.

After cooking, the cereal grains or at least one cereal grain fraction and the water are admixed with glucoamylase and glucose isomerase. The optional alpha amylase may also be added after cooking. When it is added after cooking, this may be done in addition to previously added alpha amylase. The gluooamylase and glucose isomerase may be added after cooking either simultaneously or sequentially, or both. Sequential addition of these enzymes provides for tailoring of pH and temperature to the particular enzyme. When alpha amylase is added after the cooking step, it may be prior to or simultaneously with the addition of the glucoamylase.

When the glucoamylase and glucose isomerase are added sequentially, the enzymatic treatment with glucoamylase is suitably conducted at a temperature of from about 68° F. (20° C.) to about 176° F. (80° C.) and a pH of from about 3 to about 8, preferably from about 131° F. (55° C.) to about 167° F. (75° C.) and a pH of from about 4 to about 6. The enzymatic treatment with the glucose isomerase is then suitably conducted at a temperature of from about 68° F. (20° C.) to about 212° F. (100° C.) and at a pH of from about 5 to about 9, preferably from about 131° F. (55° C.) to about 158° F. (70° C.), and a pH of from about 6 to about 8.

When the enzymatic treatment with glucoamylase and glucose isomerase is simultaneous, the conversion is suitably conducted at a temperature of from about 68° F. (20° C.) to about 176° F. (80° C.) and a pH of from about 5 to about 8, preferably at a temperature of from about 131° F. (55° C.) to about 158° F. (70° C.), and a pH of about 6 to 7. When alpha amylase is added after cooking, the treatment with the alpha amylase may suitably be up to about 3 hours, suitably at about 176° F. (80° C.) to about 194° F. (90° C.) prior to addition of the glucoamylase. After treatment with alpha-amylase, the reaction mixture is permitted to cool, as needed, to a temperature suitable for use with glucoamylase. The total treatment time or incubation period with glucoamylase and glucose isomerase is suitably up to about 48 hours, typically from about 2 hours to about 24 hours. When glucoamylase and glucose isomerase are used sequentially, treatment times may range up to about 24 hours with the glucoamylase and up to an additional 24 hours with the glucose isomerase.

In the process of the present invention, tempering of the cereal grains or at one least one cereal grain fraction occurs after cooking and during the enzymatic treatment with the optional alpha-amylase, the glucoamylase and the glucose isomerase.

The amount of water used during cooking and during enzymatic treatment with the glucoamylase and the glucose isomerase is preferably limited so that at least substantially all of the water is absorbed by the cereal grains or at least one cereal grain fraction. This reduces loss of reducing sugars to drain water. Suitably, the amount of water used during cooking and enzymatic treatment ranges from about 20% by weight to about 55% by weight based upon the total weight of water and cereal grains or cereal grain fractions. Water may be added after cooking for admixture of enzymes with the cooked cereal grains or grain fraction so as to achieve homogeneity during enzymatic treatment. After enzymatic treatment, any additional water remaining is drained. The drained, enzymatically treated cereal grains or grain fraction may optionally be tempered to distribute water substantially uniformly throughout the cereal grains prior to forming.

Enzyme concentrations for use in the present invention are defined in terms of activity as in U.S. Pat. No. 4,376,824 at column 8 line 47 to column 11 line 8. The determination of saccharides, calculation of dextrose equivalent (DE), and determination of the degree of isomerazation (% fructose) are also in accordance with the methods described in U.S. Pat. No. 4,376,824 unless otherwise indicated. See column 11 line 10 to column 12 line 43, herein incorporated by reference.

Thus, for purposes of the present invention, alpha-amylase concentration is expressed as liq/g where "g" is the grams of dry substance starch. "Liq" is short for liquefons which is an enzyme activity defined by a modification of Standard Test Method, AATCC 103-1965 "Bacterial alpha-amylase Enzymes Used in Desizing, Assay of " published in the 1967 Edition of Technical Manual of the American Association of Textile Chemists and Colorists, Volume 43, pp. B-174 and B-175.

The modifications of the published method are:

(1) The buffer solution for the starch substrate is prepared by dissolving 25.3 g of c.p. sodium hydroxide and 340 g of c.p. potassium dihydrogen phosphate in water and diluting to 2-liters.

(2) 125 ml of the buffer solution is added to the cooled, pasted starch substrate before the substrate is brought to the 500 ml volume.

(3) The pH of the starch substrate is determined and, if necessary, adjusted to 6.20±0.05.

(4) A 0.025 molar calcium chloride solution is used for enzyme sample dilution. This is prepared by dissolving 11.1 g of anhydrous c.p. calcium chloride in water and bringing the volume to 4 liters.

(5) The formula for converting from BAU to liquefons is $BAU \times 2.85 = liquefons$.

A glucoamylase activity unit (GU) is defined as the amount of enzyme which catalyzes the production of one gram of dextrose per hour at 60° C. at pH 4.5 in the procedure described below.

10 ml of a 10 percent solution of a partially hydrolyzed starch (such as Maltrin-10, a product of Grain Processing Co., Muscatine, Iowa), containing 20 mM acetate buffer at pH 4.5, is pipetted into a capped reactor maintained at 60° C. One ml of a glucoamylase solution, containing 0.03 to 0.15 GU is added and mixed therein, and the mixture maintained for one hour at 60° C. At the end of the one-hour incubation period, enzyme action is stopped by adding a predetermined volume of 1M sodium hydroxide so as to obtain a pH of 8.5 to 10.5. The mixture is then cooled to room temperature.

2.5 ml of the assay hydrolysate so obtained is pipetted into 25 ml of Fehling's solution prepared as described in method E-26 for DE determination in "Standard Analytical Methods of the Member Companies of the Corn Industry Research Foundation, Inc.", 1001 Connecticut Ave., N.W., Washington D.C. 20036. (Dextrose equivalent or DE is defined as the concentration of reducing sugars present expressed as dextrose and calculated as a percentage of the dry substance.) The mixture is brought to a boil and titrated with standard dextrose solution containing 5 g of dextrose per liter according to the procedure cited above for DE determination. A control mixture is prepared and titrated in the exact same manner as for the assay hydrolysate above except that the 1 ml of glucoamylase solution is added to the substrate solution after the one-hour incubation period and after the addition of sodium hydroxide solution. Glucoamylase activity is calculated as:

$$\frac{GU}{g} = 0.002 \, V((C - A)/W)$$

where V is the total volume (ml) of assay hydrolysate (usually 11.2 ml); C is the ml of standard dextrose solution used in the titration of the control mixture; A is the ml of standard dextrose solution used in the titration of the assay hydrolysate; and W is the weight of enzyme per ml of the diluted enzyme solution.

Glucose isomerase activity is expressed as IGIU units.

IGIU is the abbreviation for International Glucose Isomerase Unit and is that amount of enzyme which will convert 1 micromole of glucose to fructose per minute in a solution initially containing 2 moles of glucose per liter, 0.02 moles of $MgSO_4$ and 0.001 mole of $CoCl_2$ per liter at a pH of 6.84 to 6.85 (0.2M sodium maleate) and at a temperature of 60° C. Glucose isomerase determinations were carried out by the method described by N. E. Lloyd, et al., Cereal Chem., 49, No. 5, pp. 544–553 (1972).

Enzyme concentrations or dosages are expressed as liq/g, GU/g, or IGIU/g where "g" is the grams of dry substance starch initially present. Unless indicated to the contrary, it is assumed that wheat has a starch content of 63.2% by weight on a dry basis.

In the present invention, suitable enzyme concentrations are from about 1 liq/g to about 1000 liq/g for alpha-amylase, from about 0.1 GU/g to about 10 GU/g for glucoamylase, and from about 1 IGIU/g to about 100 IGIU/g for glucose isomerase. If alpha amylase is used, its concentration is preferably at least about 200 liq/g.

Enzymes for use in the present invention are commercially available. Heat stable enzymes are preferred. Suitable enzymes for use in the present invention include heat-stable alpha-amylase which is available from Novo Industry A/S, glucoamylase sold under the registered trade mark of SPEZYME GA-200, which is available from Finnish Sugar Co., Ltd., and glucose isomerase also available from Finnish Sugar Co., Ltd. and sold under the trademark SPEZYME GI.

The pH during the enzymatic treatment may be controlled with an edible buffer. An acetate buffer comprising a mixture of acetic acid and acetate is preferred. The pH may also be adjusted continuously by the use of a pH adjuster such as sodium hydroxide, potassium hydroxide, or calcium carbonate. Other buffers or pH adjusters which may be used include propionates, lactates, fumarates, malates, citrates, and phosphates, such as potassium phosphate.

After enzymatic treatment, the cereal grains or at least one cereal grain fraction may then be formed into breakfast cereal shapes by using conventional mass production cereal processing equipment. For example, the sweetened cereal grains may be shredded, flaked, extruded, or ground.

In the production of a ready-to-eat shredded cereal biscuit, suitable moisture contents of the enzymatically sweetened cereal grains for shredding range from about 28% to about 49%, more typically from about 39% to about 43% by weight, based upon the weight of the cereal grain. The cooked and tempered enzymatically sweetened cereal grains are transferred, suitably by means of belt conveyors to a hopper which feeds a screw conveyor. The latter transfers the cereal grain to a series of shredding rolls or mills via flow tubes or hoppers.

The shredding mills comprise a pair of rolls that rotate in opposite directions. One of the rolls has circumferential grooves and crosshatching grooves which are transverse to the circumferential grooves for the production of an integral net-like sheet. The spacing between the rolls is preferably controlled so as to avoid the production of webbing. Upon passing between the rolls, the cereal grain is deformed into the circumferential grooves and the crosshatching grooves. Each pair of rolls produces a cereal dough layer having a plurality of generally parallel longitudinal strands and a plurality of crosshatchings generally perpendicular to the strands. The longitudinal strands are produced by the circumferential grooves and run in parallel with the direction of movement of an underlying conveyor. The crosshatchings of the dough layer are produced by the crosshatching grooves and run generally perpendicular to the direction of movement of the conveyor.

The shredding mills are arranged in a linear series along the common underlaying conveyor. Each of the shredded dough layers or sheets are deposited on the conveyor in super-position, with their longitudinal strands running in the same direction.

The shredded cereal dough layers are continuously laminated. The laminate is cut transversely and longitudinally to the direction of flow of the product into multiple lines of biscuit preforms using known cutting devices. The cutting can be completely through the laminate to form the individual biscuit shapes prior to baking. However, cutting partially through the filled laminate to form biscuit shapes, followed by baking and separating the baked partially cut laminate into individual biscuits in known manner is preferred. This procedure provides easier control of the orientation of a cut product as it passes through the oven.

In the production of a flaked cereal, the enzymatically sweetened cereal grains may be dried to a suitable flaking moisture content and passed between large steel counter rotating cylinders having smooth surfaces. The cylinders may be internally cooled or heated. The sweetened cereal grains may be subjected to grinding prior to flaking.

Ground cereal products may be produced by subjecting the enzymatically treated cereal grains or a cereal grain fraction to drying followed by grinding in a mill. The milled product may then be toasted.

In the production of extruded products, the enzymatically sweetened cereal grains or at least one cereal grain fraction may be optionally dried to a suitable extrusion moisture content and extruded using a twin screw cooker-extruder. Various dies may be used to extrude the sweetened material into breakfast cereal shaped pieces which may be puffed or unpuffed.

In the present invention, the enzymes are inactivated to provide a shelf stable product suitably by heating during conventional baking, toasting, and drying steps. For example, in the production of a shredded biscuit product, the cut laminate may be dried, baked and toasted in conventional equipment. Suitable ovens for drying, baking and toasting the laminate include Proctor and Schwartz, Werner-Lehara, and Spooner ovens containing forced air and gas fired burners and a conveyor. Temperature profiles used in the oven for drying, baking and toasting of the biscuit preforms are generally within the range of about 200° F. to about 600° F. Temperatures within this range are generally suitable for total enzyme inactivation. The total time for drying, baking and toasting should be such so as to avoid excessive browning, particularly in view of the presence of the reducing sugars in the products of the present invention. Suitable times for drying, baking and toasting will depend upon the product thickness, product size, oven type, and amount of reducing sugars in the product. Suitable times generally range from about 4 minutes to about 10 minutes.

The amount of fructose produced in the enzymatically saccharified cereal products of the present invention should be sufficient to provide sweetness and a pleasing, complex honey-like flavor. The amount of fructose produced by the enzymatic treatment of the cereal grains or at least one cereal grain fraction should be at least 1% by weight, preferably at least about 5% by weight, based upon the total dry weight of the cereal product. It is believed that the pleasing, complex flavors and aromas of the products of the present invention are the result of Maillard reactions between fructose and cereal grain proteins. The cereal products of the present invention may have a reducing sugar content up to about 35% by weight, suitably from about 10% by weight to about 25% by weight, on a dry basis. The fructose content of the cereal products of the present invention typically ranges from about 5% to about 45%, preferably from about 15% to about 40% by weight or more, based upon the total monosaccharide content of the cereal product.

The reducing sugar content of enzymatically treated wheat samples may be determined by using a modification of the dinitrosalicylic acid (DNS) procedure of Bernfeld. Other methods for measuring reducing sugars could also be used.

To prepare samples for analyses they are ground to a relatively fine powder with a small electric coffee grinder. After grinding and blending a subsample is taken for dry solids determination.

For extraction of soluble reducing sugar a 0.3-1.0 g d.b. sample of the ground wheat is suspended in 50 ml of deionized water and stirred for two hours. Insoluble material is then removed by high speed centrifugation or filtration. Aliquots of the clear supernate or filtrate are used directly for the DNS reducing sugar procedure.

For moist samples enzyme inactivation is needed before extraction. This can be accomplished by adjusting the pH of the extraction to about 10 by adding a few drops of 10% NaOH immediately after adding the water to the ground wheat sample, or by extracting the ground sample in 50 ml of 0.02 M carbonate-bicarbonate buffer, pH 10.

The DNS reagent is prepared by dissolving 1.0 g 3.5-dinitrosalicylic acid (DNS) in 20 ml 2N NaOH and 50 ml deionized water, and adding 30 g Rochelle salt (potassium sodium tartrate). When all of the salts have dissolved water is added to a final volume of 100 ml. The reagent is stored in a stoppered brown bottle at room temperature.

A standard glucose solution (0.01 M) is prepared by dissolving 0.180 g anhydrous glucose in about 80 ml deionized water and then diluting to 100 ml. From the standard glucose solution a series of dilutions ranging in concentration from 0 to 10 uM/ml is prepared. A series of test tubes each containing 1.0 ml DNS reagent is then prepared. Into each tube is pipetted 1.0 ml of a glucose solution. Each tube is capped with a glass ball (marble) or aluminum foil and immersed in a boiling water bath for exactly five minutes. The tubes are then placed in a cold water bath for 10 minutes. Then, 10.0 ml deionized water is added to each tube and mixed well with a vortex mixer. Absorbance at 540 nm is read in a suitable colorimeter or spectrophotometer against a reagent blank (1.0 ml DNS, 1.0 ml deionized water, treated as above). The absorbance at 540 nm vs. glucose concentrations is then plotted.

Unknown samples are diluted to 1-10 uM reducing sugar/ml. Each unknown sample is treated as in the standardization procedure. Reducing sugar concentration is determined from the standard curve.

The amount of cereal starch which is converted to dextrins and reducing sugars may range up to essentially 100% by weight on a starch dry basis. However, the conversion to low molecular weight products should not be so high so as to destroy formability or machinability or to reduce final cereal product strength. In addition, the conversion to low molecular weight products should be sufficiently high so as to provide a sweetening amount of fructose.

The present invention may be used for the production of ready-to-eat breakfast cereals, instant cereals, and hot cereals.

The present invention is further illustrated in the following examples. Unless otherwise stated, enzyme dosages or concentrations are per gram of dry substance wheat starch, assuming a starch content for wheat of 63.2% by weight on a dry basis. Also, all temperatures are in degrees C., and all percentages, ratios, and proportions are by weight and the wheat is unbumped unless indicated to the contrary:

EXAMPLE I

Ready-to-eat shredded cereal biscuits naturally sweetened with fructose may be made by cooking 1000 grams of unbumped, whole wheat berries with 700 ml of water at 100° C. for 30 minutes, followed by cooling the cooked wheat to 85° C. without draining. Novo Termamyl T-120 alpha-amylase (20,000 liq/ml) may then be added to the cooked wheat in an amount of 3.2 ml (about 100 liq per gram of bone dry starch). The alpha-amylase and cooked wheat berries are then mixed thoroughly and kept at 85° C. for two hours, and then cooled to 60° C. for simultaneous addition of glucoamylase and glucose isomerase. Spezyme glucoamylase (200 GU/ml) may be added in an amount of 1.6 ml (about 0.5 GU per gram of bone dry starch). Spezyme glucose isomerase (630 IGIU/ml) may be added in an amount of 1.0 ml (about 1.0 IGIU per gram of bone dry starch). The wheat berries and the enzymes are mixed and then held at 60° C. for 18 hours. The enzymatically treated cereal grains may then be permitted to drain. The cereal grains may then be dried to a moisture content of about 41%. The cereal grains may then be shredded using counter-rotating shredding rolls, one of which is grooved, to form continuous net-like sheets. The net-like sheets may then be laminated to form a laminate of 10 layers. The laminate may then be partially cut into rectangular, spoon-sized biscuit preforms. The preforms may then be dried, baked, and toasted in a gas-fired zone oven for about 7 minutes at temperatures ranging from inlet to outlet within the range of about 200° F. to about 600° F., and then separated into individual biscuits to obtain a product having a moisture content of about 4.5% by weight.

EXAMPLE II

Ready-to-eat shredded cereal biscuits naturally sweetened with fructose may be made as in Example I except after addition of the glucoamylase and glucose isomerase, the wheat berries and enzymes may be held at 60° C. for two hours instead of 18 hours.

EXAMPLE III

Ready-to-eat shredded cereal biscuits naturally sweetened with fructose may be made as in Example I except the 3.2 ml (100 liq/g) of alpha-amylase may be added to the cook water, followed by addition of the wheat berries. After the cook, the wheat berries are held at 85° C. for two hours, and cooled to 60° C. for addition of glucoamylase and glucose isomerase as in Example I.

EXAMPLE IV

Ready-to-eat shredded cereal biscuits naturally sweetened with fructose may be made as in Example III except after addition of the glucoamylase and glucose isomerase, the wheat berries and enzymes may be held at 60° C. for two hours instead of 18 hours.

EXAMPLE V

Ready-to-eat shredded cereal biscuits naturally sweetened with fructose may be made as in Example I except: (a) the cooked wheat may be cooled to 21° C. instead of 85° C. without draining, (b) the alpha-amylase is omitted, and (c) the cooled wheat is heated to 60° C. after about 2 hours at 21° C. for addition of the glucoamylase and glucose isomerase.

EXAMPLE VI

Ready-to-eat shredded cereal biscuits naturally sweetened with fructose may be made as in Example II except: (a) one half of the alpha-amylase (50 liq./g) is added to the cook water, followed by addition of wheat berries, and the remaining half of the alpha-amylase (50 liq./g) is added to the cooked wheat, (b) the glucoamylase is added in an amount of 3.2 ml (about 1.0 GU/g) instead of 1.6 ml (about 0.5 GU/g), and (c) the glucose isomerase is added in an amount of 0.5 ml (about 0.5 IGIU/g) instead of 1.0 ml (about 1.0 IGIU/g).

EXAMPLE VII

Ready-to-eat shredded cereal biscuits naturally sweetened with fructose may be made as in Example II except: (a) the wheat berries may be presoaked with 1.6 ml of the alpha-amylase (50 liq./g), and (b) the amount of the alpha-amylase added to the cooked wheat is reduced from 3.2 ml (100 liq./g) to 1.6 ml (50 liq./g).

EXAMPLE VIII

Ready-to-eat shredded cereal biscuits naturally sweetened with fructose may be made by cooking 1000 grams of unbumped, whole wheat berries with 700 ml of water at 210° F. for 30 minutes, followed by cooling the cooked wheat to 60° C. without draining for addition of glucoamylase and glucose isomerase. Spezyme glucoamylase (200 GU/ml) may be added in an amount of 32.0 ml (about 10.0 GU per gram of bone dry starch). The glucoamylase and wheat berries are mixed and then held at 60° C. for about 4 hours. Then, Spezyme glucose isomerase (630 IGIU/ml) in an amount of 5.0 ml (about 5.0 IGIU per gram of bone dry starch) is buffered to a pH of 7.0 with a 1.0M potassium phosphate buffer. The mixture of cooked wheat berries and glucoamylase is admixed with the buffered glucose isomerase then held at 60° C. for 14 hours. The enzymatically treated cereal grains may then be permitted to drain. The cereal grains may then be dried to a moisture content of about 41%, and shredded, cut, dried, baked, and toasted as in Example I.

EXAMPLE IX

Ready-to-eat cereal flakes naturally sweetened with fructose may be made by drying the drained, enzymatically sweetened cereal grains of Example VIII to a moisture content of about 20% by weight instead of 41%, flaking the dried wheat berries between flaking rolls, and then toasting the flakes at a temperature of about 275° F. in a toasting drum oven to inactivate the enzymes and to produce a toasted, fructose sweetened product.

EXAMPLE X

This Example demonstrates the potential loss of reducing sugars which are produced during enzymatic cooking of wheat in an amount of water which is substantially greater than can be absorbed by the wheat.

Twenty grams of clean, soft, white wheat, i.e., about 18.46 g d.b., was mixed with 27 mls of water. The water was dosed with 0.185 ml of Termamyl T-120 alpha amylase containing 1850 liquefons. This mixture of wheat, water and enzyme was immersed in a boiling water bath for 30 minutes. A control was also set up which contained no alpha-amylase but was otherwise treated in the same manner as described above. After cooking, the wheat was drained for 15 minutes in a sintered glass funnel and aspirated for an additional 30 minutes under laboratory vacuum. The liquid drained from the wheat was collected and analyzed for reducing sugar. Next, the wheat samples were ground in a laboratory mill and thoroughly blended. The material was then sampled for a dry solids determination. Next, the blended material was extracted exhaustively with water and the extracts were analyzed for reducing sugar by the dinitrosalicylic acid procedure of Bernfield. [Bernfield P. (1955) in Method in Enzymology (Colowick, S. P. and Kaplan, H. O., ed.) Vol. 1, p. 149, Academic Dress, New York] The Bernfield procedure was calibrated against anhydrous dextrose. The data collected from this procedure are set out in Table 1:

TABLE 1

| | Reducing Sugar (% db.) | | |
| --- | --- | --- | --- |
| | Ground Wheat | Drain Water | Total |
| Control | 0.51 | 0.02 | 0.53 |
| alpha-amylase Treated | 0.54 | 0.17 | 0.71 |

Enzymatic hydrolysis of starches results in producing soluble reducing sugars which tend to leach into the aqueous solution surrounding the wheat. This loss of reducing sugar is undesirable in terms of potential sweetening effect and, additionally, causes an increase in the biological oxygen demand of the process drain water.

EXAMPLE XI

This example demonstrates the effect of various alpha-amylase treatments on whole wheat starch hydrolysis.

Six trials were performed wherein the water added for the cooking in each assay was reduced from 1.35 mls per gram of wheat (Example X) to 0.76 mls. per gram of wheat. Additionally, three different strategies for alpha-amylase addition and hydrolysis were employed, each using two different alpha-amylase dosages (Termamyl T-120), i.e., 100 and 200 liq/g starch. In trials 1 and 2, whole, clean wheat was added to preheated water followed by the addition of alpha-amylase. The mixture was immersed in a boiling water bath and cooked for 30 minutes. After cooking, the wheat was drained into a sintered glass funnel for 15 minutes and aspirated with laboratory vacuum for an additional 30 minutes. A dry solids determination was made upon the sample. The wheat was then suspended in a 20 milimolar acetate buffer, having a pH of 3.0. The material was then ground in a blender to prepare samples which were assayed for reducing sugar concentrations. The drain water was also analyzed for reducing sugar.

In trials 3 and 4, the wheat was cooked in the same manner as in trials 1 and 2. After the cooking step, the undrained wheat was allowed to cool to 80° C. and incubated for two hours at 80° C. before draining, drying, and blending. In trials 3 and 4, no drain water was collected because the wheat retained all the moisture.

In trials 5 and 6, the wheat was presoaked at room temperature after the addition of alpha-amylase. After three hours of soaking, the wheat was cooked and handled as in trials 1 and 2. In trials 1, 3 and 5 the alpha-amylase concentration was 100 liq/g and in trials 2, 4 and 6 the alpha-amylase concentration was 200 liq/g. The results of trials 1 through 6, showing approximate enzyme treatment times, are illustrated in Table 2.

TABLE 2

EFFECT OF VARIOUS ALPHA-AMYLASE TREATMENTS ON WHEAT STARCH HYDROLYSIS

| Trial | Dosage Liq/g | Drain Vol. ml | Reducing Sugar % db. | | | Time (hrs) |
| --- | --- | --- | --- | --- | --- | --- |
| | | | Wheat | Drain | Total | |
| 1 | 100 | 2.3 | 0.32 | 0.05 | 0.37 | 1.25 |
| 2 | 200 | 2.5 | 1.34 | 0.06 | 1.40 | 1.25 |
| 3 | 100 | 0 | 0.83 | 0 | 0.83 | 2.5 |
| 4 | 200 | 0 | 1.88 | 0 | 1.88 | 2.5 |
| 5 | 100 | 2.0 | 0.83 | 0.10 | 0.93 | 4.25 |
| 6 | 200 | 3.2 | 2.05 | 0.14 | 2.19 | 4.25 |

Trials 5 and 6, involving presoaking at room temperature for 3 hours, produced the most total reducing sugar. It is believed the presoaking allows the wheat to imbibe moisture and alpha-amylase before being subjected to the cooking temperatures. It is noted, however, that a significant portion of the reducing sugar was lost in the drain water in this procedure and enzyme contact times were the longest. In contrast, trials 3 and 4, where the cooked wheat was incubated at 80° C. before the drain and dry step resulted in slightly lower degrees of hydrolyses with no loss of either drain water or reducing sugar with substantially shorter contact times. Thus, it has been shown that thermo-stable alpha-amylase can be used effectively in the wheat cooking step to hydrolyze part of the wheat starch to dextrins.

EXAMPLE XII

This example demonstrates the effect of various glucoamylase treatments on hydrolysis of alpha-amylase treated whole wheat starch.

Five trials were performed including a control. In each trial, 20 grams of wheat was dosed with alpha-amylase (Termamyl T-120) at a concentration of 200 liq/g starch and soaked for one hour at room temperature before a 30-minute cook in a boiling water bath using about 0.75 ml of water per gram of wheat. In the control trial, the wheat was drained and dried after the cook. In the rest of the trials, the undrained wheat was allowed to cool to 58° C., whereupon the cooled undrained wheat was dosed with 1.0 ml glucoamylase (Spezyme GA) containing 58.3 GU or a dosage of 5 GU/g dry wheat starch. This mixture was then incubated for various periods of time at 58° C. before draining and drying. After sampling for dry solids determinations the wheat was ground, suspended in 20 millimolar acetate buffer having a pH of 3, and boiled to terminate enzyme activity. The material was then centrifuged to remove insoluble material. The various supernatants were analyzed for reducing sugar. The results of Example III are set out in Table 3:

TABLE 3

| Trial | Reducing Sugar % db | Percent Hydrolysis* |
| --- | --- | --- |
| Control - No GA | 0.77 | 1.1 |
| GA - 2 hrs. | 12.36 | 17.6 |
| GA - 4 hrs. | 13.21 | 18.8 |
| GA - 10 hrs. | 14.61 | 20.8 |
| GA - 22 hrs. | 16.91 | 24.1 |

*Based on a starch content of 63.2% (702 mg potential reducing sugar per gram of wheat.)

The results depicted in Table 3 show that the glucoamylase was rapidly absorbed by the cooked wheat. After only two hours of incubation at 58° C. a reducing sugar level of 12.36% db. was obtained. Thus, about 17 percent of the starch was hydrolyzed to reducing sugar. Longer incubations resulted in further reducing sugar generation. At 22 hours, the starch was about 24 percent hydrolyzed.

Portions of the wheat treated with glucoamylase for four or ten hours were ground and dried in a 90° C. forced-air oven for one hour. The drying samples emitted a pleasant sweet aroma somewhat reminiscent of honey. A sample of wheat which had been cooked in the conventional manner without addition of enzymes was also dried in a similar manner. The dried, treated samples had a rich golden-brown color, while the untreated sample retained a pale straw color after drying. The taste of the treated sample was perceptibly sweeter and more complex than that of the untreated sample or a commercial shredded wheat sample.

EXAMPLE XIII

This example demonstrates the production of sweetening amounts of reducing sugars using lower alpha-amylase and glucoamylase concentrations than in Example XII by the additional use of glucose isomerase.

Six trials were run where the cooking step was performed with reduced water levels of about 0.75 ml of water per gram of wheat.

In trial 1, no alpha-amylase was added for the cooking step. After cooking, the wheat was cooled to 60° C, dosed with 1.0 ml of enzyme solution containing 58.3 GU of glucoamylase (Spezyme GA) (0.5 GU/g) and 11.6 IGIU of glucose isomerase, (Spezyme GI) (1 IGIU/g), and incubated for two hours at 60° C.

In trial 2, no alpha-amylase was added for the cooking step. The wheat was cooked and then incubated for two hours at 60° C. with glucoamylase at a concentration of 2.0 GU/g and glucose isomerase at a concentration of 2.5 IGIU/g.

In trial 3, alpha-amylase was added to the cooking step in a concentration of 100 liq/g. The wheat was cooked and then incubated for two hours at 60° C. with glucoamylase at a concentration of 0.5 GU/g and glucose isomerase at a concentration of 1.0 IGIU/g.

In trial 4, alpha-amylase (Termamyl T-120) was added to the cooking step at a concentration of 100 liq/g. The wheat was cooked and then incubated for two hours at 60° C. with glucoamylase at a concentration of 2.0 GU/g and glucose isomerase at a concentration of 2.5 IGIU/g.

In trial 5, both alpha-amylase and glucoamylase were added to the cooking step at a concentration of 100 liq/g and 0.5 GU/g respectively. The wheat was cooked and then incubated for two hours at 60° C. without further enzyme addition.

In trial 6, alpha-amylase was added to the cooking step in the concentration of 200 liq/g. The wheat was cooked and then incubated for two hours at 60° C. with glucoamylase at a concentration of 5 GU/g and glucose isomerase at a concentration of 5 IGIU/g.

In each trial, after the two-hour incubation at 60° C., the wheat was divided into two equal portions. The first portion was immediately drained and dried at 90° C. in a forced-air oven. The second portion was tempered at room temperature for 16 hours before draining and drying. Portions of each of the dried samples were ground and sampled for solids determinations and reducing sugar concentrations. The results are depicted in Table 4:

TABLE 4

| Trial | Enzyme Conc. | | | Percent of Reducing Sugar* | |
|---|---|---|---|---|---|
| | Alpha (liq/g) | GA (GU/g) | GI (IGIU/g) | Non-Tempered | Tempered |
| 1 | 0 | 0.5 | 1.0 | 2.0 | 2.8 |
| 2 | 0 | 2.0 | 2.5 | 3.0 | 5.0 |
| 3 | 100 | 0.5 | 1.0 | 2.6 | 4.8 |
| 4 | 100 | 2.0 | 2.5 | 3.9 | 6.7 |
| 5 | 100 | 0.5 | 0 | 2.2 | 3.9 |
| 6 | 200 | 5.0 | 5.0 | — | 13.2 |

*Grams of reducing sugar (expressed as glucose) per 100 grams dried wheat.

The results show that the sugar content of the tempered samples was consistently higher than that of the non-tempered samples. This result indicates that some enzyme activity remained after the 100° C. cook and 60° C. incubation steps. Samples of the ground, dried wheat were tasted and compared to a sample of ground commercial shredded wheat. The perceived sweetness of each sample correlated reasonably well with the reducing sugar content of each sample. The sugar content for the 18-hour sample from trial 6 is equivalent to about ½ teaspoon of sugar per 1 ounce serving of cereal. The sweetness of the sample was readily apparent and may be greater than that needed for a naturally sweetened cereal. The 18-hour sample from trial 5, where no glucose isomerase was used and the glucoamylase was added to the cook, had virtually no perceptible sweetness. The use of glucose isomerase results in perceptible sweetness at lower reducing sugar levels than when glucoamylase is used without it as in trial 5 and in Example XII.

EXAMPLE XIV

This example demonstrates the increase in reducing sugar production over that obtained in Example XIII when: (a) alpha-amylase treatment after cooking is conducted at 85° C. instead of 60° C. and, (b) glucoamylase and glucose isomerase treatment is at 60° C. for 18 hrs instead of 2 hrs followed by 16 hours at room temperature.

In trial 1, a control was run where no enzyme was added. The wheat was oooked with about 1.39 ml of water per gram of wheat at about 100° C. for 30 minutes.

In trial 2, no enzyme was added for the cooking step. The wheat was cooked and then incubated for two hours at 85° C. with alpha-amylase (Termamyl T-120) at a concentration of 100 liq/g. After the incubation step, the mixture was allowed to cool to 60° C. whereupon 1.0 ml of solution containing 58.3 GU of Spezyme GA glucoamylase (0.5 GU/g) and 1.7 IGIU of Spezyme GI glucose isomerase (1.0 IGIU/g) was added to the cooled mixture. The cooled mixture was then incubated at 60° C. for either 2 or 18 hours.

In trial 3, alpha-amylase was added to the cooking step at a concentration of 50 liq/g. After the cooking step, more alpha-amylase was added to the mixture at a concentration of 50 liq/g which was then allowed to incubate for two hours at 85° C. The mixture was cooled to 60° C. and the glucoamylase and glucose isomerase were added as in trial 2.

In trial 4, wheat was presoaked with alpha-amylase at a concentration of 50 liq/g for two hours at 60° C. After the cooking step, more amylase was added at a concentration of 50 liq/g and the wheat was treated as in trial 3.

In trial 5, alpha-amylase was added to the cooking step at a concentration of 100 liq/g. After the cooking step, the wheat was incubated for two hours at 85° C. without further alpha-amylase addition. The wheat was then allowed to cool to 60° C. and glucoamylase and glucose isomerase were added as in trial 2.

In trial 6, alpha-amylase was added to the cooking step in the concentration of 50 liq/g. After the cooking step, additional amylase was added to the mixture at a concentration of 50 liq/g which was then incubated for two hours at 85° C. The mixture was then allowed to cool to 60° C. whereupon glucoamylase at a concentration of 1.0 GU/g and glucose isomerase at a concentration of 0.5 IGIU/g were added to the mixture which was then allowed to incubate at 60° C. for either 2 or 18 hours.

In trials 2 through 5 the amount of water used for cooking was about one-half of the water level used in trial 1. In trial 6, the amount of water used for cooking was about two-thirds of the water level used in trial 1.

After treatment as set out in trials 1 through 6 the wheat was drained and dried for two hours in a forced-air oven at 90° C. The wheat was then ground and blended whereupon samples were taken for dry solids determinations, reducing sugar analyses and sensory evaluations. The results are depicted in Table 5.

TABLE 5

| | Dosage | | Percent of Reducing Sugar | |
|---|---|---|---|---|
| Trial | (liq/g) | GA (GU/g) | GI(IGIU/g) | 2 Hours | 18 Hours |
| 1 | 0 | 0 | 0 | 0 | — |
| 2 | 100 | 0.5 | 1.0 | 11.1 | 17.2 |
| 3 | 100 | 0.5 | 1.0 | 8.7 | 12.7 |
| 4 | 100 | 0.5 | 1.0 | 9.7 | 14.2 |
| 5 | 100 | 0.5 | 1.0 | 6.9 | 14.3 |
| 6 | 100 | 1.0 | 0.5 | 14.0 | 21.5 |

The results of Example XIV show that significant hydrolysis of the starch in the wheat to reducing sugars was achieved in all of the assays except the control. This was especially true after 18 hours of incubation. The most reducing sugar was produced in trial 6 where more than 21 percent reducing sugar was produced. All of the 18-hour samples except trial 1, had readily apparent sweetness and pleasing, complex, honey-like flavors. It is believed that the flavors are the result of Maillard reactions between reducing sugars, especially fructose, and other components in the cooked grain during the high temperature drying.

EXAMPLE XV

This example demonstrates the effect of glucoamylase dosage on reducing sugar production in whole wheat with or without alpha-amylase addition to the cook.

In this investigation eight trials were set up. Trials 1, 2 and 3 were set up in the absence of any alpha-amylase. All the trials of this Example were low water cooks, i.e., 75 ml of water to 100 gms of wheat. After the cooking step, the wheat was cooled to 60° C. and dosed with 1.0 ml of Spezyme GA glucoamylase solution containing the appropriate amount of enzyme activity. In the first trial, glucoamylase was added at a concentration of 2 GU/g. In trial 2, glucoamylase was added at a concentration of 5 GU/g. In trial 3, glucoamylase was added at a concentration of 10 GU/g. The wheat was allowed to incubate at 60° C. with the glucoamylase and periodic samples were taken for reducing sugar analyses.

In trials 4 and 5, alpha-amylase (Termamyl T-120) was added for the cooking steps at a concentration of 50 liq/g. In trial 4, glucoamylase was added at a concentration of 2 GU/g. In trial 5, glucoamylase was added at a concentration of 5 GU/g. As with trials 1, 2 and 3, the wheat was incubated at 60° C. and periodic samples were taken for reducing sugar analyses.

In trials 6 and 7, alpha-amylase was added to the cooking step at a concentration of 100 liq/g. After the cooking step in trial 6, the wheat was cooled to 60° C. and dosed with glucoamylase at a concentration of 2 GU/g. In trial 7, the wheat was cooled to 85° C. and held for three hours before cooling to 60° C., whereupon glucoamylase was added at a concentration of 2 GU/g and periodic samples were taken for reducing sugar analyses.

In trial 8, alpha-amylase was added to the cooking step at a concentration of 200 liq./g. After the cooking step, the wheat was cooled to 60° C. and dosed with glucoamylase at a concentration of 2 GU/g. The wheat was incubated at 60° C. and periodic samples were taken for reducing sugar analyses. Table 6 presents the reducing sugar percentages for trials 1-8:

TABLE 6

| | | Percent Reducing Sugar | | | | |
|---|---|---|---|---|---|---|
| Assay | Dosage | 3 Hrs. | 6 Hrs. | 10 Hrs. | 22 Hrs. | 46 Hrs. |
| 1 | 0 liq - 2 GU | 2.88 | 6.54 | 8.72 | 16.61 | 18.09 |
| 2 | 0 liq - 5 GU | 3.51 | 6.76 | 12.23 | 19.87 | 26.67 |
| 3 | 0 liq - 10 GU | 4.70 | 10.28 | 15.73 | 23.95 | 36.39 |
| 4 | 50 liq - 2 GU | 3.12 | 5.45 | 7.98 | 16.33 | 17.41 |
| 5 | 50 liq - 5 GU | 3.34 | 7.35 | 11.18 | 16.70 | 31.00 |
| 6 | 100 liq - 2 GU | 3.14 | 6.51 | 8.37 | 13.81 | 24.84 |
| 7 | 100 liq - 2 GU | 7.07 | 13.64 (7 Hrs.) | — | 21.29* | 35.21** |
| 8 | 200 liq - 2 GU | 4.11 | 6.82 | 10.74 | 21.74 | 30.11 |

*19 hours
**43 hours

These data indicate that significant amounts of reducing sugar can be produced without the use of alpha-amylase. Low doses of alpha-amylase, i.e., 50 liq/g. or less, had no significant effect on the amount of reducing sugar produced by a constant glucoamylase dosage. In trials 1-3, where no alpha-amylase was used and significant levels of reducing sugars were produced, a glucoamylase dosage of only 2 GU/g of starch, produced 16.6 percent reducing sugar, i.e., 16.6 gms. per 100 gms. of wheat, in 22 hours at 60° C. Higher glucoamylase dosages increased the rate of production of reducing sugars.

The results of trials 3-8 show the effect of various alpha-amylase dosages upon reducing sugar production when used in combination with glucoamylase. With lower alphaamylase dosages, i.e., 50-100 liq/g. reducing sugar production tended to be about the same or decrease when alpha-amylase was used with a 60° C. incubation. For example, reducing sugar production with a glucoamylase dosage of 2 GU/g was about the same with or without the alpha-amylase addition (trials 1, 4, and 6). Reducing sugar production was increased with a higher alpha-amylase dosage of 200 liq/g. or with a dosage of 100 liq/g. if a 3-hour 85° C. incubation step was included after the cooking step and prior to the addition of any glucoamylase.

In trial 7, an amylase dosage of 100 liq/g. and an 85° C. incubation step produced more than 21 percent reducing sugar in 19 hours incubation with a glucoamylase concentration of 2 GU/g. The 19-hour sample from trial 7 was found to have a very sweet taste. An incubation at 85° C. as in trial 7, followed by a shorter, 60° C. incubation of only 7–10 hours may be used to produce a sufficiently sweet grain.

EXAMPLE XVI

This example demonstrates the effect of glucose isomerase and pH on reducing sugar distribution when alpha-amylase is not added for the enzyme saccharification of wheat.

In this example, two enzyme-treatment trials were performed without alpha-amylase addition. Twenty grams of whole wheat was oooked at about 100° C. in an amount of water of about 0.75 ml per gram of wheat for 30 minutes.

In trial 1, after the cooking step, the wheat was cooled and incubated 16 hours at 60° C. solely with glucoamylase at a dosage of 10 GU/g of starch by addition of 1 ml glucoamylase solution containing 200 GU per ml.

In trial 2, after the cooking step, the wheat was incubated at 60° C. with both glucoamylase and glucose isomerase at doses of 10 GU/g and 10 IGIU/g, respectively. Two milliliters of glucose isomerase (100 IGIU/ml) was added in a 1.0M phosphate buffer, at pH of 7.0.

In trial 2 the glucoamylase was added first, whereupon the mixture was incubated for 16 hours at a pH of about 5.3 to 5.8 before adding the glucose isomerase. This strategy was used to allow the glucoamylase enzyme to hydrolyze some of the starch to glucose under more optimal pH conditions before adding the isomerase at the higher pH. After incubation with glucose isomerase for 24 hours at 60° C., the wheat was oven-dried, ground and then sampled for analyses of sugars by liquid chromatography. The results are presented in Table 7:

TABLE 7

| Trial | Carbohydrate Composition % of Wheat dry basis | |
|---|---|---|
| | Dextrose | Fructose |
| 1 | 16.97 | 0.78 |
| 2 | 10.91 | 6.13 |

EXAMPLE XVII

This example demonstrates the preparation of an enzyme sweetened bran cereal, formed by extrusion.

100 grams of Red Wheat bran (about 14% by weight starch, dry basis) and 100 grams of White Wheat heavy bran (about 60% by weight starch, dry basis) were mixed together. The starch content was about 37% by weight based upon the total weight of the brans (dry basis). After adding 200 grams of water, the mass was cooked at 100° C. for 30 minutes to gelatinize the starch. After cooling to 65° C, Spezyme GA200 glucoamylase (200 GU/gram) was added in an amount of 5 grams (about 5 GU/gram bran). The glucoamylase and bran were mixed and then held for 60 minutes at 65° C. Then, sufficient magnesium hydroxide (about 1 g/100 g bran) was added to adjust and maintain the pH at about 7.5 after which 0.6 ml Spezyme GI glucose isomerase (3600 IGIU/ml) was added to give an enzyme concentration of about 10.8 IGIU/gram bran. The mixture of bran and enzyme was then held, for an additional 60 minutes at 65° C. The sweetened bran cereal was then cooked at 121° C. for 15 minutes and extruded through ⅛" holes using a Hobart A200 mixer equipped with a meat grinder/extruder. The strands so formed were dried at 100° C. to produce the final product with a moisture content of about 1.5% to about 3% by weight. The dried product had a sugar content, by liquid chromatography, of about 11% glucose, 5% fructose, 3% maltose, and 1% other sugars, with sufficient residual starch and high molecular weight dextrin (about 17%) for formability. The residual starch and high molecular weight dextrin content was calculated by difference, based upon the 37% by weight starch content of the bran mixture (dry basis).

What is claimed is:

1. A method for producing an enzyme-saccharified cereal product, comprising:
   (a) cooking cereal grains or at least one cereal grain fraction with water to at least partially gelatinize cereal starch;
   (b) treating the cooked cereal grains or at least one cereal grain fraction of step (a) with water and enzymes comprising glucoamylase and glucose isomerase under conditions to produce fructose while retaining a sufficient amount of starch or high molecular weight dextrins for formability of the enzyme treated cereal grain or at least one enzyme treated cereal grain fraction into a breakfast cereal shape;
   (c) forming the enzyme treated cereal grain or the at least one enzyme treated cereal grain fraction of step (b) into a breakfast cereal shape; and
   (d) inactivating the enzymes, the amount of fructose produced being sufficient to provide a sweet taste to the cereal product.

2. A method as claimed in claim 1 wherein whole cereal grains are cooked in step (a), and the cooked grains retain discreteness during the enzymatic treatment of step (b).

3. A method as claimed in claim 2 wherein the discrete enzymatically treated cereal grains are formed by shredding.

4. A method as claimed in claim 2 wherein the discrete enzymatically treated cereal grains are formed by flaking.

5. A method as claimed in claim 2 wherein the discrete enzymatically treated cereal grains are formed by grinding.

6. A method as claimed in claim 1 wherein the at least one enzymatically treated cereal grain fraction or the enzymatically treated cereal grains are formed by extrusion.

7. A method as claimed in claim 1 wherein the amount of water present during the enzymatic treatment of the cereal grains or at least one grain fraction is limited so that at least substantially all of the water is absorbed by the cereal grain or the at least one grain fraction to retain fructose in the cereal product.

8. A method as claimed in claim 7 wherein the amount of water present during the enzymatic treatment ranges from about 20 percent by weight to about 55 percent by weight based upon the total weight of the water and the weight of the cereal grains or at least one grain fraction.

9. A method as claimed in claim 1 wherein the amount of fructose produced by the enzymatic treatment is at least about 5% by weight, based upon the total dry solids of the cereal product.

10. A method as claimed in claim 1 wherein in step (a), the cereal grains or at least one cereal grain fraction comprises bran.

11. A method as claimed in claim 1 wherein the enzymatic treatment and the cooking are partially simultaneous.

12. A method as claimed in claim 11 wherein the enzymatic treatment comprises cooking the cereal grain or at least one grain fraction in the presence of alpha-amylase to convert a portion of the cereal starch to dextrins, and then subjecting the cooked product to glucoamylase and glucose isomerase to produce fructose.

13. A method as claimed in claim 12 wherein prior to cooking, the cereal grain or at least one grain fraction is soaked in the presence of alpha-amylase.

14. A method as claimed in claim 12 wherein the cooked product is subjected to glucoamylase and glucose isomerase simultaneously.

15. A method as claimed in claim 12 wherein the alpha-amylase is used in an amount of from about 1 liq/g to about 1,000 liq/g., glucoamylase is used in an amount of from about 0.1 GU/g to about 10 GU/g, and the glucose isomerase is used in an amount of from about 1 IGIU/g to about 100 IGIU/g.

16. A method as claimed in claim 1 wherein the enzymatic treatment with the glucoamylase and glucose isomerase takes place at a temperature of from about 68° F. (20° C.) to about 176° F. (80 ° C.) and at a pH of from about 5 to about 8.

17. A method as claimed in claim 13 wherein the soaking is at a temperature of from about 68° F. (20° C.) to about 212° F. (100° C.) and a pH of from about 5 to 8.

18. A method as claimed in claim 12 wherein the cooking is at a temperature of from about 176° F. (80° C.) to about 212° F. (100° C.) and a pH of from about 5 to about 8, and the enzymatic treatment with the glucoamylase and glucose isomerase takes place at a temperature of from about 68° F. (20° C.) to about 176° F. (80 ° C.) and at a pH of from about 5 to about 8.

19. A method as claimed in claim 12 wherein the enzymatic treatment with the glucoamylase and glucose isomerase takes place at a temperature of from about 131° F. (55° C.) to about 158° F. (70° C.) and a pH of from about 6 to 7.

20. A method as claimed in claim 12 wherein the reducing sugar content of the cereal product ranges from about 10% by weight to about 25% by weight of total dry solids, and the amount of fructose is from about 5 percent by weight to about 45 percent by weight, based upon the total monosaccharide content of the cereal product.

21. A method as claimed in claim 1 wherein the enzymatic treatment comprises subjecting the cooked cereal grain or grain fraction to alpha-amylase, glucoamylase and glucose isomerase to produce fructose.

22. A method as claimed in claim 21 wherein the cereal grain or grain fraction is first subjected to alpha-amylase and then to glucoamylase and glucose isomerase.

23. A method as claimed in claim 22 wherein the cereal grain or grain fraction is subjected to alpha-amylase during cooking, additional alpha-amylase is added after cooking and then the glucoamylase and glucose isomerase are added to produce fructose.

24. A method as claimed in claim 23 wherein the enzymatic treatment with the glucoamylase and glucose isomerase takes place at a temperature of from about 68° F. (20° C.) to about 176° F. (80° C.) and at a pH of from about 5 to about 8.

25. A method as claimed in claim 23 wherein the glucoamylase and glucose isomerase are added sequentially, the enzymatic treatment with the glucoamylase takes place at a temperature of from about 68° F. (20° C.) to 176° F. (80° C.), and a pH of from about 3 to about 8, and the enzymatic treatment with the glucose isomerase takes place at a temperature of from about 68° F. (20° C.) to about 212° F. (100° C.) and at a pH of from about 5 to about 9.

26. A method as claimed in claim 23 wherein whole cereal grains are cooked in step (a) and the cooked grains retain discreteness during the enzymatic treatment with alpha-amylase, glucoamylase, and glucose isomerase.

27. A method as claimed in claim 26 wherein the whole cereal grains are malted.

28. A method as claimed in claim 26 wherein the discrete enzymatically treated cereal grains are formed by shredding, and the enzymes are inactivated by baking the shreds.

29. A method as claimed in claim 4 wherein the enzymes are inactivated by toasting the flakes.

30. A method as claimed in claim I wherein the enzymatically treated product obtained in step (b) is dried prior to forming into a breakfast cereal shape.

31. A method for producing an enzyme-saccharified ready-to-eat cereal product, comprising:
(a) cooking whole cereal grains to at least partially gelatinize cereal starch;
(b) treating the cooked cereal grains of step (a) with water and enzymes comprising glucoamylase and glucose isomerase under conditions to produce a sweetening amount of fructose while retaining the cooked cereal grains in discrete form;
(c) forming the enzyme treated cereal grains of step (b) into a breakfast cereal shape; and
(d) inactivating the enzymes, the fructose content of the cereal product being at least about 1% by weight of the total dry solids of the cereal product.

32. A method as claimed in claim 31 wherein the inactivation of the enzymes comprises heating the formed cereal grain.

33. A method as claimed in claim 32 wherein the discrete enzymatically treated cereal grains are formed by shredding.

34. A method as claimed in claim 33 wherein the enzymatically treated cereal grains are shredded into integral net-like sheets, the sheets are laminated, the laminate is cut, and the cut laminate is baked to inactivate the enzymes.

35. A method as claimed in claim 32 wherein the enzymatic treatment comprises cooking the cereal grain in the presence of alpha-amylase to convert a portion of the cereal starch to dextrins, and then subjecting the cooked product to glucoamylase and glucose isomerase to produce fructose.

36. A method as claimed in claim 35 wherein the alpha-amylase is used in an amount of from about 1 liq/g to about 1,000 liq/g., glucoamylase is used in an amount of from about 0.1 GU/g to about 10 GU/g, and the glucose isomerase is used in an amount of from about 1 IGIU/g to about 100 IGIU/g, the cooking is at a temperature of from about 176° F. (80° C.) to about 212° F. (100° C.) and a pH of from about 5 to about 8, and the enzymatic treatment with glucoamylase and glucose isomerase takes place at a temperature of from about 68° F. (20° C.) to about 176° F. (80° C.) and at a pH of from about 5 to about 8.

37. A method as claimed in claim 36 wherein the amount of fructose is from about 5 percent by weight to about 45 percent by weight, based upon the total monosaccharide content of the cereal product.

38. A method for producing an enzyme-saccharified ready-to-eat cereal product, comprising:
   (a) cooking a cereal grain fraction to at least partially gelatinize cereal starch;
   (b) treating the cooked grain fraction with water and enzymes comprising glucoamylase and glucose isomerase under conditions to convert a portion of the cereal starch to a sweetening amount of fructose while retaining a sufficient amount of starch or high molecular weight dextrins for formability of the enzyme treated cereal grain fraction into a breakfast cereal shape;
   (c) forming the enzyme treated cereal grain fraction into a breakfast cereal shape; and
   (d) inactivating the enzymes, the fructose content of the cereal product being at least about 1% by weight of the total dry solids of the cereal product.

39. A method as claimed in claim 38 wherein the cereal grain fraction is wheat bran flour.

40. A method as claimed in claim 39 wherein the enzymes further comprise alpha-amylase.

41. A method as claimed in claim 39 wherein the enzymatic treatment is at least partially prior to the cooking.

42. A method as claimed in claim 39 wherein the enzyme treated cereal grain fraction is formed into pieces by extrusion.

43. A method as claimed in claim 39 wherein the starch content of the bran flour is from about 25% to about 45% by weight, on a dry basis.

44. A method as claimed in claim 38 wherein the enzymatically treated product obtained in step (b) is dried prior to forming into a breakfast cereal shape.

* * * * *